US011099168B2

(12) United States Patent
Xie et al.

(10) Patent No.: US 11,099,168 B2
(45) Date of Patent: Aug. 24, 2021

(54) METHODS AND APPARATUS FOR WATER DETECTION IN MULTIPHASE FLOWS

(71) Applicant: Schlumberger Technology Corporation, Sugar Land, TX (US)

(72) Inventors: Cheng-Gang Xie, Singapore (SG); Massimiliano Fiore, Singapore (SG)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 172 days.

(21) Appl. No.: 16/042,177

(22) Filed: Jul. 23, 2018

(65) Prior Publication Data

US 2020/0025743 A1  Jan. 23, 2020

(51) Int. Cl.
| | |
|---|---|
| *G01N 33/28* | (2006.01) |
| *G01F 1/58* | (2006.01) |
| *G01F 1/74* | (2006.01) |
| *G01N 22/04* | (2006.01) |
| *G01N 27/22* | (2006.01) |

(52) U.S. Cl.
CPC ......... *G01N 33/2847* (2013.01); *G01F 1/584* (2013.01); *G01F 1/74* (2013.01); *G01N 22/04* (2013.01); *G01N 27/221* (2013.01); *G01N 27/223* (2013.01)

(58) Field of Classification Search
CPC ........ G01N 22/00; G01N 22/26; G01N 22/28; G01N 22/2823; G01R 27/02; G01R 27/08; G01R 27/14; G01R 27/26; G01R 27/2605; G01F 1/56–60
See application file for complete search history.

(56) References Cited

U.S. PATENT DOCUMENTS

| | | | | |
|---|---|---|---|---|
| 5,736,637 | A | * | 4/1998 | Evans .................... G01N 27/06 73/152.31 |
| 5,854,820 | A | | 12/1998 | Slijkerman et al. |
| 6,831,470 | B2 | | 12/2004 | Xie et al. |
| 7,469,188 | B2 | * | 12/2008 | Wee ......................... G01F 1/58 702/45 |

(Continued)

FOREIGN PATENT DOCUMENTS

| | | |
|---|---|---|
| WO | 2008030912 A2 | 3/2008 |
| WO | 2009101392 A1 | 8/2009 |

(Continued)

OTHER PUBLICATIONS

International Search Report and Written Opinion issued in the related PCT Application PCT/US2019/042800 dated Oct. 24, 2019 (7 pages).

(Continued)

*Primary Examiner* — Douglas X Rodriguez
*Assistant Examiner* — David B Frederiksen
(74) *Attorney, Agent, or Firm* — Cameron R. Sneddon

(57) ABSTRACT

Methods and apparatus for detecting water in multiphase flows are disclosed. An example apparatus includes a conduit including an inlet to receive a multiphase flow and an electromagnetic sensor coupled to a liquid-rich region of the conduit to measure a permittivity of the multiphase flow, and a water detection manager to determine that water is detected in the multiphase flow based on the permittivity.

19 Claims, 7 Drawing Sheets

(56) References Cited

U.S. PATENT DOCUMENTS

| | | | |
|---|---|---|---|
| 7,503,227 B2 * | 3/2009 | Davis | G01F 1/66 |
| | | | 73/861.42 |
| 7,631,543 B2 | 12/2009 | Wee | |
| 8,076,950 B2 | 12/2011 | Wee | |
| 8,224,588 B2 | 7/2012 | Wee | |
| 8,522,534 B2 | 9/2013 | Yoshida et al. | |
| 8,536,883 B2 | 9/2013 | Xie et al. | |
| 8,570,050 B2 | 10/2013 | Nyfors | |
| 8,686,745 B2 | 4/2014 | Kirkaune | |
| 9,528,869 B2 | 12/2016 | Xie et al. | |
| 9,588,071 B2 | 3/2017 | Nyfors | |
| 9,638,556 B2 | 5/2017 | Xie et al. | |
| 9,645,130 B2 | 5/2017 | Xie et al. | |
| 2007/0151806 A1 * | 7/2007 | Boyle | G01N 33/2888 |
| | | | 184/6.21 |
| 2008/0319685 A1 | 12/2008 | Xie et al. | |
| 2010/0064820 A1 * | 3/2010 | David | G01N 22/00 |
| | | | 73/861.04 |
| 2011/0291845 A1 * | 12/2011 | Rice | G08B 21/20 |
| | | | 340/605 |
| 2013/0110411 A1 | 5/2013 | Black et al. | |
| 2013/0144548 A1 * | 6/2013 | Xie | G01F 1/60 |
| | | | 702/65 |
| 2013/0327154 A1 | 12/2013 | Xie et al. | |
| 2014/0331783 A1 * | 11/2014 | Xie | G01F 1/662 |
| | | | 73/861.04 |
| 2015/0346117 A1 | 12/2015 | Nyfors | |
| 2016/0131601 A1 * | 5/2016 | Sharma | G01N 33/2823 |
| | | | 324/642 |
| 2017/0160069 A1 * | 6/2017 | Folgero | G01N 27/06 |
| 2018/0364083 A1 * | 12/2018 | Janssens | G01N 9/002 |

FOREIGN PATENT DOCUMENTS

| | | |
|---|---|---|
| WO | WO2015185450 A1 | 12/2015 |
| WO | 2018160927 A1 | 9/2018 |

OTHER PUBLICATIONS

Kjetil Folgerø, Andreas Linge Tomren, Stig Frøyen, Permittivity calculator. Method and tool for calculating the permittivity of oils from PVT data, 30th International North Sea Flow Measurement Workshop Oct. 23-26, 2012 (15 pages).

* cited by examiner

|  | Permittivity (relative) | Conductivity [S/m] | Comments |
|---|---|---|---|
| Gas | 1.0 – 1.1 | 0.0 | Pressure and temperature dependent |
| Oil | 2.0 – 2.7 | ~0.0 | Light to heavy oil; pressure, temperature, and measurement-frequency dependent |
| Water/brine | ~80 – ~20 | ~0 – ~80 | Temperature 20-120°C NaCl salinity 0 – 260 kppm |

FIG. 2

```
int getWaterDetection { if ((ε_max(Δt) - ε_min(Δt)) > ((ε_oil(p,T) - ε_gas(p,T)) + δε_noise)
        {
                waterDetectionFlag = True;    //Water is present
        }
elseif (ε_max(Δt) > (ε_oil(p,T) + δε_oil)
        {
                waterDetectionFlag = True;    //Water is present
        }
else
        {
                waterDetectionFlag = False;   //Water is absent
        }
return waterDetectionFlag;
}
```

METHODS AND APPARATUS FOR WATER DETECTION IN MULTIPHASE FLOWS

BACKGROUND

This disclosure relates generally to hydrocarbon production and, more particularly, to methods and apparatus for water detection in multiphase flows.

DESCRIPTION OF THE RELATED ART

Most oil-gas wells produce a mixture of oil, water, and gas. During hydrocarbon production, a determination of flow rates of individual phases (e.g., oil, gas, water, etc.) of a multiphase flow is desirable. The individual phase flow rates can be derived from the measured phase volume fractions and phase flow velocities. A determination of other properties of the multiphase mixture is also desirable, including the presence and salinity of produced water or injected water. Such properties can be used to determine information about the mixture and may affect other measurements being made on the multiphase mixture.

SUMMARY

Certain aspects of some embodiments disclosed herein are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

An example apparatus includes a conduit including an inlet to receive a multiphase flow and an electromagnetic sensor coupled to a liquid-rich region of the conduit to measure a permittivity of the multiphase flow, and a water detection manager to determine that water is detected in the multiphase flow based on the permittivity.

An example method includes determining a first permittivity and a second permittivity of a multiphase flow based on electromagnetic data obtained from an electromagnetic sensor, comparing a difference between the first permittivity and the second permittivity to a water detection threshold, and in response to the difference satisfying the water detection threshold, generating an alert indicating that water is detected in the multiphase flow.

An example non-transitory computer readable storage medium comprising instructions which, when executed, causes a machine to at least determine a first permittivity and a second permittivity of a multiphase flow based on electromagnetic data obtained from an electromagnetic sensor, compare a difference between the first permittivity and the second permittivity to a water detection threshold, and generate an alert indicating that water is detected in the multiphase flow when the difference satisfies the water detection threshold.

Various refinements of the features noted above may exist in relation to various aspects of the present embodiments. Further features may also be incorporated in these various aspects as well. These refinements and additional features may exist individually or in any combination. For instance, various features discussed below in relation to the illustrated embodiments may be incorporated into any of the above-described aspects of the present disclosure alone or in any combination. Again, the brief summary presented above is intended just to familiarize the reader with certain aspects and contexts of some embodiments without limitation to the claimed subject matter.

BRIEF DESCRIPTION OF THE DRAWINGS

FIG. 2 depicts an example table including example parameters associated with a multiphase flow.

FIG. 5 depicts example machine readable instructions that may be executed to implement the example water detection manager apparatus of FIGS. 1 and/or 3 that may be used to implement the examples disclosed herein.

The figures are not to scale. Wherever possible, the same reference numbers will be used throughout the drawing(s) and accompanying written description to refer to the same or like parts.

DETAILED DESCRIPTION

Figure 1:
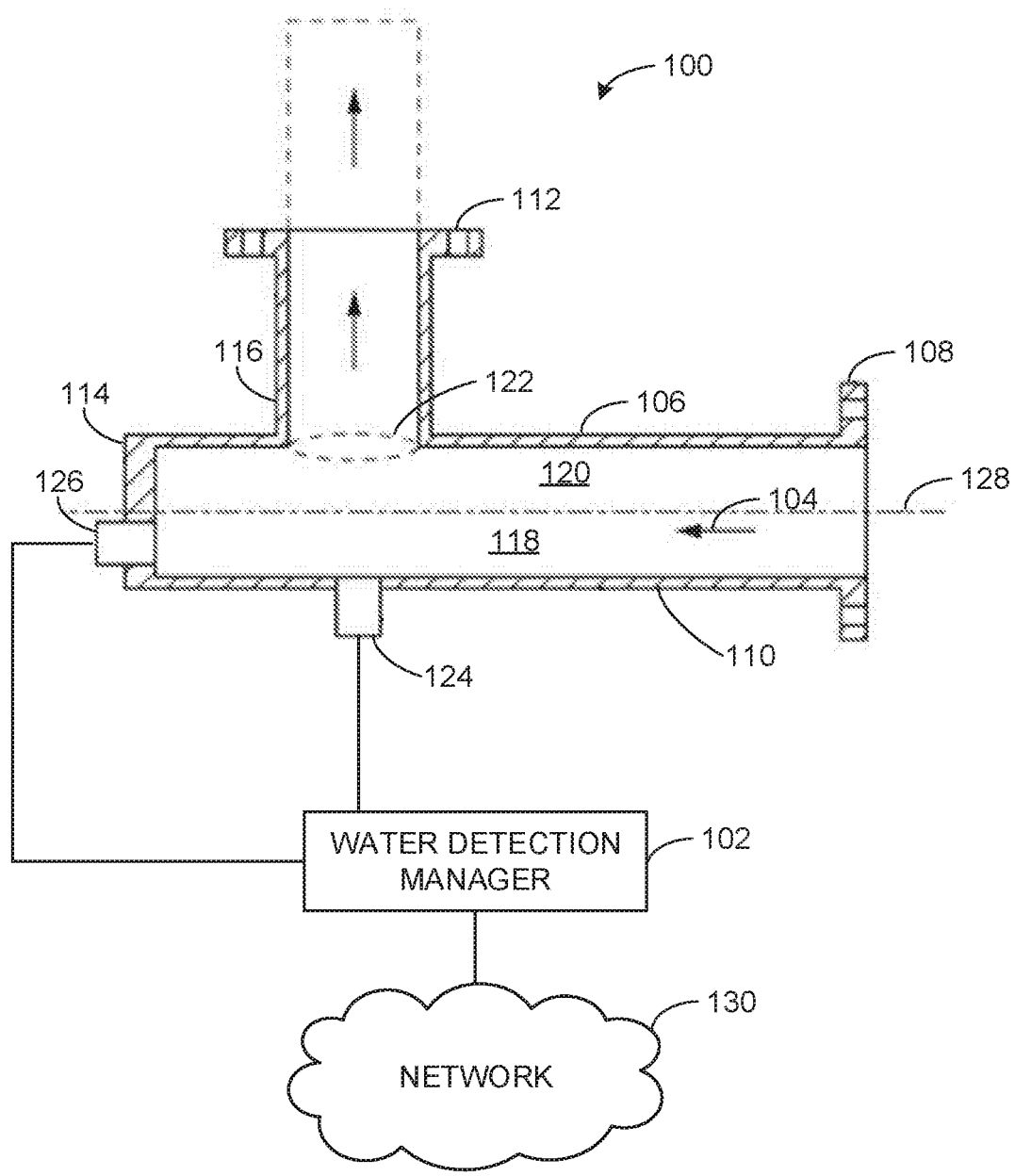
FIG. 1 illustrates an example multiphase flow measurement system including an example water detection manager apparatus for determining liquid properties of a multiphase flow.

It is to be understood that the present disclosure provides many different embodiments, or examples, for implementing different features of various embodiments. Specific examples of components and arrangements are described below for purposes of explanation and to simplify the present disclosure. These are, of course, merely examples and are not intended to be limiting.

When introducing elements of various embodiments, the articles "a," "an," "the," and "said" are intended to mean that there are one or more of the elements. The terms "comprising," "including," and "having" are intended to be inclusive and mean that there may be additional elements other than the listed elements. Moreover, any use of "top," "bottom," "above," "below," other directional terms, and variations of these terms is made for convenience, but does not mandate any particular orientation of the components.

Most oil-gas wells produce oil, gas, and water from an earth formation. For example, a flow of fluid including oil, gas, and water is considered a three-phase flow, or a multiphase flow or multiphase mixture. In such examples, the three-phase flow includes one gas phase corresponding to the gas component of the flow and two liquid phases corresponding to the oil and water components of the flow. It is desirable during an oilfield operation (e.g., well test operation, an oil and/or gas production operation, etc.) to perform flow measurements to determine the flow rates of individual phases of the multiphase flow. In particular, measurement of the volume fractions and flow velocities of for example, oil, gas, and water in a conduit, such as a pipe, is highly desirable. It is also desirable to determine properties of the multiphase mixture, such as the presence and salinity of water in the mixture, as this provides information about the mixture and may affect other measurements being made on the multiphase mixture.

In general, a determination of properties of a multiphase flow can be difficult due to a wide variety of flow regimes the multiphase flow can exhibit. For example, three phases of a multiphase flow can be mixed together with one phase as the continuous phase and the remaining two phases dispersed within the multiphase flow. Primarily, there is phase separation between gas and liquid with the liquid often moving at a much lower velocity than the gas.

Additionally, flow phase and velocity distributions of a multiphase flow may alter both spatially and temporally. Sudden or gradual variation in flow rates of one phase or another may cause a change in flow regime. Also, due to the high pressure encountered deep underground or below seabed, a flow that is mixed or in bubble-flow regime can become dominated by a discernible high gas fraction as the pressure drops nearer the ground or subsea surface and the gas expands and/or comes out of solution.

Prior implementations to measure multiphase flows used multiphase flowmeters and sensors to determine properties of the multiphase flows. In some prior implementations, the multiphase flowmeters included electromagnetic (EM) sensors such as radiofrequency (RF) and/or microwave sensors, electrical (e.g., capacitance, conductance) impedance sensors, to measure some of the properties including a permittivity and/or a conductivity of the multiphase flow through a conduit (e.g., a pipe). In such implementations, the multiphase flowmeter measured the permittivity and/or the conductivity at liquid-rich region(s) of the conduit (e.g., in the underside of a horizontal blind-tee section, in a near-wall region (e.g., a near inner-wall region) of a vertical pipe section). The multiphase flowmeter typically determined properties of the liquid phase of the multiphase flow including water conductivity (salinity). However, these prior implementations did not teach the determination a presence of water in the multiphase flow or in a wet-gas flow stream.

Examples disclosed herein include water detection manager apparatus to detect a presence of water in a multiphase flow and/or a wet-gas flow stream. In some disclosed examples, the water detection manager apparatus detects the presence of water by determining a mixture permittivity and/or a mixture conductivity of the multiphase flow. In some disclosed examples, the water detection manager apparatus determines the mixture permittivity and/or the mixture conductivity by obtaining measurements from one or more EM sensors at a high data acquisition rate (e.g., 5 kilohertz (kHz) measurement rate, 10 kHz measurement rate, etc.). In some disclosed examples, the one or more EM sensors include an RF/microwave open-coaxial probe (e.g., a microwave frequency open-coaxial reflection probe), an RF/microwave local transmission measurement sensor, etc.

In some disclosed examples, one or more probes are installed at a liquid-rich region of a horizontal blind-tee end-flange, or at a vertical pipe near wall region, or at a vertical pipe end-flange to obtain the sensor measurements. Example water detection manager apparatus disclosed herein can detect the presence of water in either horizontal or vertical conduits. For flow-assurance purposes, detecting the presence of water in multiphase flows is important for oilfield operations (e.g., providing an alert of the risk of the formation of hydrates in the flow line) when a flow-stream water-to-liquid ratio (WLR) is very low and/or a gas volume fraction (GVF) is very high. In some disclosed examples, the water detection manager apparatus can set a WLR measured by a multiphase flowmeter (e.g., a dual-energy gamma-ray based multiphase flowmeter (MPFM)) to zero to avoid and/or otherwise prevent reporting of non-physical (e.g., negative) time-averaged WLR values and, thus, improve an accuracy or a confidence in flow rate measurements of oil and gas phases in a multiphase flow.

FIG. 1 illustrates an example multiphase flow measurement system 100 including an example water detection manager 102 to determine liquid properties of a multiphase flow 104. In FIG. 1, the multiphase flow measurement system 100 includes an example blind tee 106. The blind tee 106 of FIG. 1 includes an example inlet 108, a first example conduit 110, an example outlet 112, an example end (flange) section 114, and a second example conduit 116. In FIG. 1, the first conduit 110 is a horizontal blind tee conduit and the second conduit 116 is a vertical blind tee conduit. At the downstream of the outlet 112, a multiphase flowmeter may be installed (not shown in FIG. 1).

In operation, the multiphase flow 104 enters the blind tee 106 through the inlet 108, travels along the first conduit 110, through the second conduit 116, and out through the outlet 112. The end section 114 operates as a barrier that forces the movement of the multiphase flow 104 into the second conduit 116. In general, the blind tee 106 is configured so that the first conduit 110 is approximately horizontal and the second conduit 116 is approximately vertical. In some examples, the horizontal orientation of the first conduit 110 enables an example bottom section 118 of the first conduit 110 to be liquid rich and an example upper section 120 of the first conduit 110 to be gas rich. Alternatively, the flow in the second conduit 116 may not flow vertically upward, but may be arranged to flow vertically downward, or at another angle relative to the first conduit 110.

In some examples, the bottom section 118 of the first conduit 110 includes liquid rich regions even in multiphase flows with high gas-to-liquid ratios (e.g., wet gas with gas volume fraction (GVF) >95%). In some examples, liquid rich regions can be produced in the blind tee 106 proximate the end section 114 and/or beneath an example opening 122 of the second conduit 116. In some examples, the first conduit 110 can be about 5 meters or less in length (e.g., 0.5 meters, 1.5 meters, 2.5 meters, etc.). Alternatively, the first conduit 110 may be more than 5 meters in length. In some examples, more pronounced liquid rich regions can be produced when the end section 114 and the opening 122 are separated by a section of the first conduit 110, as illustrated in FIG. 1.

In the illustrated example of FIG. 1, a first example electromagnetic (EM) sensor 124 or a second example EM sensor 126 is disposed below a central axis 128 of the first conduit 110. In FIG. 1, the EM sensor(s) 124, 126 are coupled to the water detection manager 102. Alternatively, the EM sensor(s) 124, 126 may be disposed above the central axis 128. In FIG. 1, the first EM sensor 124 is coupled to the first conduit 110 and is disposed in the bottom section 118 directly below the opening 122. In FIG. 1, the second EM sensor 126 is coupled to the end section 114 of the first conduit 110 and is disposed in the bottom section 118. Additionally or alternatively, one or more of the EM sensors 124, 126 may be disposed on the underside of the first conduit 110, in the bottom section 118, and/or coupled with the end section 114 below the central axis 128. Additionally or alternatively, EM sensor(s) 124, 126 may be installed at the liquid-rich region of a vertical pipe end flange, or at the near inner-wall liquid-rich region of a vertical pipe section.

In the illustrated example of FIG. 1, the water detection manager 102 can determine properties of the liquid phase (e.g., water conductivity/salinity, water volume fraction, WLR, etc.) of the multiphase flow 104 based on the positioning of the EM sensor(s) 124, 126 in the blind tee 106 as depicted in FIG. 1 and/or in other examples as described above. In some examples, the water detection manager 102 can determine the properties of the gas phase (e.g., permittivity change with pressure and/or temperature) of the multiphase flow 104 based on alternative positions of the EM sensor(s) 124, 126 or in combination with additional EM sensor(s) coupled to the blind tee 106. For example, the water detection manager 102 can determine the gas phase properties based on one or more of the EM sensors 124, 126 being disposed on the topside of the first conduit 110, in the upper section 120 above the central axis 128, near the inlet 108, etc. In other examples, in addition to the EM sensor(s) 124, 126, additional EM sensor(s) can be disposed on the topside of the first conduit 110, in the upper section 120 above the central axis 128, near the inlet 108, etc.

In FIG. 1, the water detection manager 102 determines the properties of the liquid phase of the multiphase flow 104 that is present in a shallow measurement zone (e.g., about 2 millimeters (mm) depth of investigation) of the EM sensor(s) 124, 126, by obtaining sensor measurements from the EM sensor(s) 124, 126. In FIG. 1, the EM sensor(s) 124, 126 are RF/microwave frequency open-coaxial (reflection) probes (e.g., substantially similar to sensors described in U.S. Pat. No. 9,638,556, entitled "COMPACT MICROWAVE WATER-CONDUCTIVITY PROBE WITH INTEGRAL SECOND PRESSURE BARRIER," filed Dec. 16, 2015, which is incorporated by reference herein in its entirety). Alternatively, the EM sensor(s) 124, 126 may be RF/microwave-based magnetic-dipole antennas, RF/microwave local transmission measurement antennas, RF/microwave local resonance measurement antennas, millimeter-wave sensors, or electrical impedance (e.g., capacitance, conductance, etc.) measurement electrodes or probes (e.g., an electrical impedance local measurement sensor).

In the illustrated example of FIG. 1, the EM sensor(s) 124, 126 measure, at one or more chosen measurement frequencies, one or more properties of the multiphase flow 104. For example, the EM sensor(s) 124, 126 can perform sensor measurements (e.g. reflection measurements of amplitude-attenuation and phase-shift of the reflected RF signals relative to those of the incident signals) of the multiphase flow 104 and generate electromagnetic data based on the sensor measurements. The water detection manager 102 can obtain the electromagnetic data from the EM sensor(s) 124, 126 and determine a dielectric constant, or a permittivity (e.g., an electrical permittivity, a fluid permittivity, etc.), and/or a conductivity (e.g., an electrical conductivity, a fluid conductivity, etc.) of the multiphase flow 104 based on the electromagnetic data.

In some examples, the water detection manager 102 determines a presence of water in the multiphase flow 104 based on values of permittivity and/or conductivity of the water phase being substantially higher than those of the hydrocarbon phase(s) (e.g., gas and/or oil), as shown in an example table 200 depicted in FIG. 2. In the table 200 of FIG. 2, a gas (e.g., a gas phase) has an example (relative) permittivity range of 1.0-1.1. The relative permittivity of the table 200 represents a ratio of an absolute permittivity of a material relative to the absolute permittivity of vacuum. In the table 200 of FIG. 2, oil (e.g., an oil phase) has an example (relative) permittivity range of 2.0-2.7. In the table 200 of FIG. 2, water (e.g., a water phase) has an example (relative) permittivity of approximately 80 at 20 degrees Centigrade (deg C.) with no salt content, and NaCl-based brines have example (relative) permittivities in the range approximately [20, 80] depending on NaCl mass concentration dissolved in brine (i.e. salinity) and temperature. For example, pure water with no salt content (salinity zero) can have a relative permittivity of approximately 80 at 20 deg C. In such examples, at the same temperature of 20 deg C., the relative permittivity of water can decrease from approximately 80 to approximately 45 as the NaCl salt mass concentration in water (or salinity) increases to 260 kppm (thousand parts per million, or 26%). At the same salinity, brine relative permittivity decreases with increasing temperature.

In the illustrated example of FIG. 2, the table 200 depicts example conductivity values in Siemens per meter (S/m) for gas, oil, and water/brine. In the table 200 of FIG. 2, gas has an example conductivity of 0.0 S/m, oil has an example conductivity of approximately 0.0 S/m, water has an example conductivity of approximately 0.0 S/m with no salt content (and at DC or a low measurement frequency), and NaCl-based brines have example conductivities in the range approximately [0, 80] S/m depending on NaCl mass concentration dissolved in brine and temperature. For example, pure water with no salt content can have a conductivity of approximately 0 S/m at 20 deg C. In such examples, at the same temperature of 20 deg C., the conductivity of the water can increase from approximately 0 S/m to approximately 25 S/m as the salt concentration increases to 260 kppm. NaCl-based brine conductivity changes approximately 2% per deg C. temperature change.

As noted in the table 200 of FIG. 2, the permittivity for gas is pressure (p) and temperature (T) dependent. For example, the dielectric constant of methane gas increases with pressure at a fixed temperature. For example, at a pressure of approximately 100 bar and 100 deg C., the dielectric constant of methane gas is 1.07. Also noted in the table 200 of FIG. 2, the permittivity values and/or ranges are given for light to heavy oil and are pressure, temperature, and measurement frequency dependent. Further noted in the table 200 of FIG. 2, the permittivity and conductivity values for water/brine correspond to temperatures in a range of 20 to 120 deg C. and where a range of salinity of sodium chloride (NaCl) is 0 to 260 kppm.

In some examples, the water detection manager 102 of FIG. 1 can detect a presence of water based on the permittivity and conductivity values of the water phase being substantially higher than the gas and oil phases as shown in the table 200 of FIG. 2. For example, the water detection manager 102 can calculate a permittivity value of the multiphase flow 104 local to the EM sensor(s) 124, 126 and determine that the multiphase flow 104 includes water based on the calculated (flow mixture) permittivity value being substantially higher (e.g., more than 5 times higher, etc.) than the permittivity values of FIG. 2 for the gas and oil phases. In other examples, the water detection manager 102 can calculate a conductivity value of the multiphase flow 104 and determine that the multiphase flow 104 includes brine based on the calculated (flow mixture) conductivity value being substantially higher than a conductivity threshold value (e.g., higher than 0.5 S/m etc.).

Turning back to FIG. 1, the water detection manager 102 can obtain EM sensor (raw) measurement data, or EM data, at substantially high data acquisition frequencies (e.g., 5 kHz, 10 kHz, etc.). For example, the water detection manager 102 can include RF and/or microwave measurement electronics to rapidly acquire RF and/or microwave measurement data from the EM sensor(s) 124, 126. The water detection manager 102 can process the EM data substantially instantaneously (e.g., at 5 Hz, 10 Hz, 15 Hz, etc.) to calculate mixture parameters associated with the multiphase flow 104 over a moving (e.g., rolling) short-time window (e.g., a time window of $\Delta t=50$ ms, 100 ms, 1000 ms, etc.). Alternatively, the water detection manager 102 can process the EM data at any other specified processing rate. For example, there are at least one hundred EM data samples rapidly acquired over each short-time window $\Delta t$, for the water detection manager 102 to calculate one or more mixture parameters that represent a characteristic and/or a quantification of the multiphase flow 104 local to a measurement zone of the EM sensor(s) 124, 126, as described below in mixture parameters (1)-(8):

Mixture Parameter (1): Mixture Permittivity Average ($\varepsilon_{avg}(\Delta t)$)
Mixture Parameter (2): Mixture Permittivity Minimum ($\varepsilon_{min}(\Delta t)$)
Mixture Parameter (3): Mixture Permittivity Maximum ($\varepsilon_{max}(\Delta t)$)
Mixture Parameter (4): Mixture Permittivity Standard Deviation ($\varepsilon_{std}(\Delta t)$)
Mixture Parameter (5): Mixture Conductivity Average ($\sigma_{avg}(\Delta t)$)
Mixture Parameter (6): Mixture Conductivity Minimum ($\sigma_{min}(\Delta t)$)
Mixture Parameter (7): Mixture Conductivity Maximum ($\sigma_{max}(\Delta t)$)
Mixture Parameter (8): Mixture Conductivity Standard Deviation ($\sigma_{std}(\Delta t)$)

Additionally or alternatively, the water detection manager 102 can calculate fewer or more mixture parameters than the mixture parameters (1)-(8) as described above. Additionally or alternatively, the water detection manager 102 can determine other parameters, for example the water-detection occurrence frequency over a relatively long duration of time (e.g., number of positive water-detection events calculated every 60 seconds(s)), and the water salinity (e.g. determined based on one or more of Mixture Parameters (1)-(8) above, such as the ratio of the water-rich Mixture Conductivity Maximum to the water-rich Mixture Permittivity Maximum).

In the multiphase flow measurement system 100 of FIG. 1, the water detection manager 102 is communicatively coupled to an example network 130. The network 130 of the illustrated example of FIG. 1 is the Internet. However, the network 130 can be implemented using any suitable wired and/or wireless network(s) including, for example, one or more data buses, one or more Local Area Networks (LANs), one or more wireless LANs, one or more cellular networks, one or more private networks, one or more public networks, etc. In some examples, the network 130 enables the water detection manager 102 to be in communication with another multiphase flow measurement system 100 and/or with an external computing device (e.g., a database, a server, etc.) coupled to the network 130.

In some examples, the network 130 enables the water detection manager 102 to communicate with the external computing device to store the information obtained and/or processed by the water detection manager 102. In such examples, the network 130 enables the water detection manager 102 to retrieve and/or otherwise obtain the stored information for processing.

In the illustrated example of FIG. 1, the water detection manager 102 generates a report including one or more mixture parameters associated with the multiphase flow 104 and transmits the report to another computing device via the network 130. For example, the network 130 can be a cloud-based network, which can perform cloud-based data storage, analytics, big data analysis, deep machine learning, etc., to enable multi-well, multi-field reservoir-scale modeling, digital oilfield high-efficiency operations and automation, oil-gas production management and/or optimization based on information obtained and/or processed by the water detection manager 102. In some examples, the water detection manager 102 can be an Internet of Things (IoT) device enabled to facilitate capturing, communicating, analyzing, and acting on data generated by networked objects and machines.

In some examples, the water detection manager 102 generate an alert such as displaying an alert on a user interface, propagating an alert message throughout a process control network (e.g., transmitting an alert to another computing device via the network 130), generating an alert log and/or an alert report, etc. For example, the water detection manager 102 can generate an alert corresponding to a characterization of the multiphase flow 104 including a detection of water in the multiphase flow 104.

Figure 3:
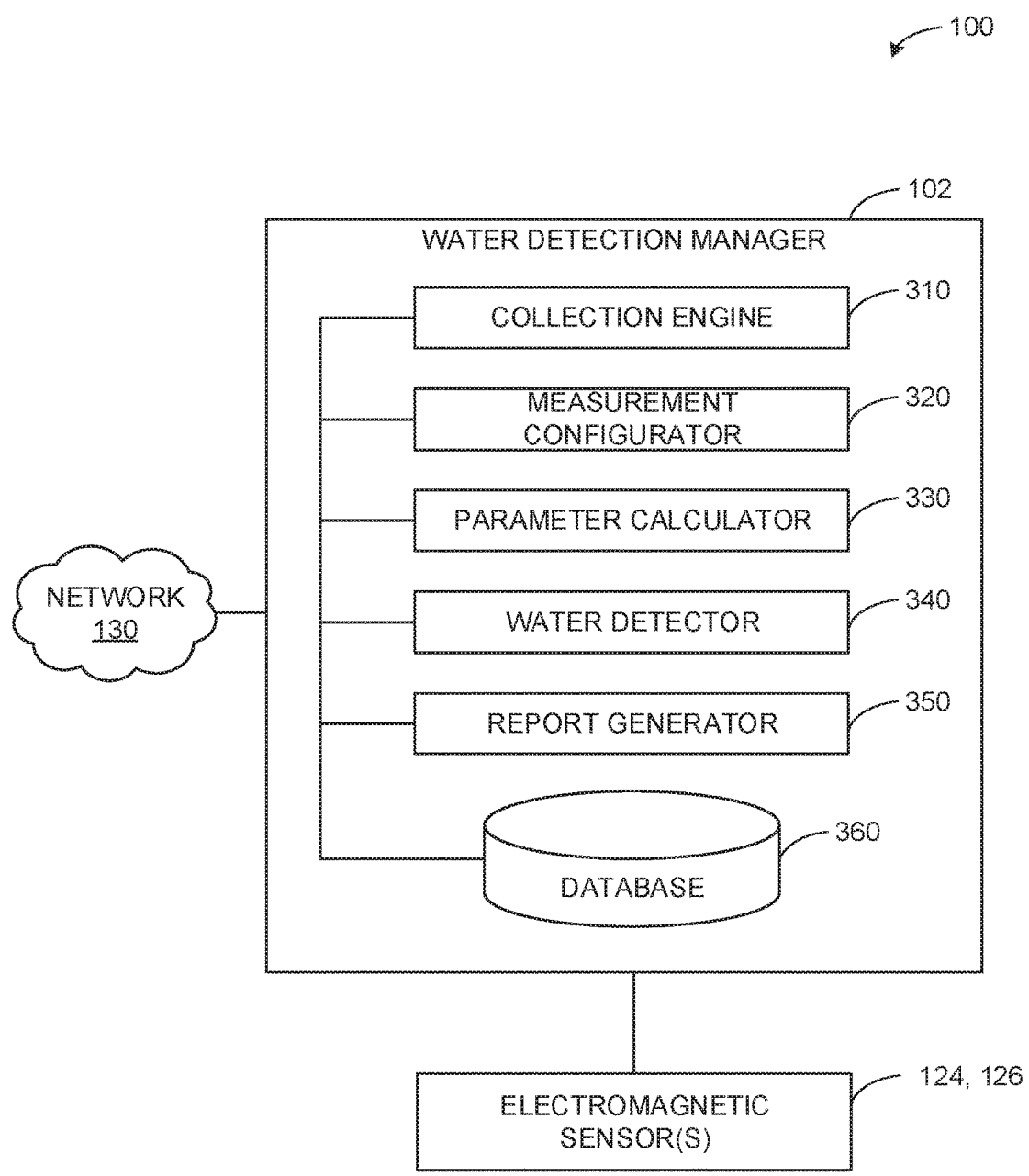
FIG. 3 is a block diagram of an example implementation of the example multiphase flow measurement system of FIG. 1 including the example water detection manager apparatus of FIG. 1.

FIG. 3 is a block diagram of an example implementation of the multiphase flow measurement system 100 of FIG. 1 including the water detection manager 102 of FIG. 1. The water detection manager 102 obtains EM data from the EM sensor(s) 124, 126 and calculates one or more mixture parameters associated with the multiphase flow 104 of FIG. 1 based on the EM data. The water detection manager 102 can detect a presence of water in the multiphase flow based on the one or more mixture parameters. The water detection manager 102 can generate and transmit a report including the one or more mixture parameters and/or the water detection determination result to another computing device via the network 130. Additionally or alternatively, the water detection manager 102 can generate and propagate based on the one or more mixture parameters and/or the water detection determination result to another computing device via the network 130. In FIG. 3, the water detection manager 102 includes an example collection engine 310, an example measurement configurator 320, an example parameter calculator 330, an example water detector 340, an example report generator, and an example database 360.

In the illustrated example of FIG. 3, the water detection manager 102 includes the example collection engine 310 to control a device and/or receive data from the device communicatively coupled to the water detection manager 102. For example, the collection engine 310 can implement RF/microwave sensor electronics to receive and/or otherwise obtain data from the EM sensor(s) 124, 126. In some examples, the collection engine 310 instructs the EM sensor(s) 124, 126 to transmit data to the collection engine 310. In other examples, the collection engine 310 receives data from the EM sensor(s) 124, 126 without instructing the EM sensor(s) 124, 126 to transmit the data. In some examples, the collection engine 310 controls the EM sensor(s) 124, 126 by directing the EM sensor(s) 124, 126 to excite a signal at a specified frequency (e.g., a measurement frequency). For example, the EM sensor(s) 124, 126 can operate at one measurement frequency or a plurality of measurement frequencies.

In the illustrated example of FIG. 3, the water detection manager 102 includes the measurement configurator 320 to adjust an operation of a device communicatively coupled to the water detection manager 102 and/or a configuration used by the parameter calculator 330 to calculate mixture parameters. In some examples, the measurement configurator 320 adjusts an operation of one or both EM sensors 124, 126 by decreasing or increasing an excitation frequency of one or both EM sensors. In some examples, the measurement configurator 320 adjusts an acquisition frequency of the collection engine 310. In some examples, the measurement configurator 320 changes a processing frequency, a type of measurement window used (e.g., a moving window, an exponential moving average, etc.), and/or a measurement window interval ($\Delta t$) used by the parameter calculator 330 to calculate mixture parameters associated with the multiphase flow 104 of FIG. 1.

In the illustrated example of FIG. 3, the water detection manager 102 includes the parameter calculator 330 to calculate and/or otherwise determine one or more mixture parameters associated with the multiphase flow 104 of FIG. 1. For example, the parameter calculator 330 can calculate one or more of the mixture parameters (1)-(8) as described above at a processing frequency. For example, the parameter calculator 330 can determine the mixture parameters (1)-(8) every 50 ms, 100 ms, 1000 ms, etc., and/or any other processing frequency.

In the illustrated example of FIG. 3, the water detection manager 102 includes the water detector 340 to determine a presence of water in the multiphase flow 104 based on one or more mixture parameters associated with the multiphase flow 104. In some examples, the water detector 340 compares a permittivity (e.g., a maximum permittivity, a minimum permittivity, etc.) of the multiphase flow 104 to a water detection threshold and determines that water is present based on the comparison. For example, the water detector 340 can determine that the permittivity satisfies the water detection threshold based on the permittivity being substantially greater (e.g., more than twice) than the oil permittivity, or other the water detection threshold.

In some examples, the water detector 340 compares a permittivity difference to the water detection threshold and determines that water is present based on the comparison. For example, the permittivity difference can be a difference between a maximum permittivity ($\varepsilon_{max}$) and a minimum permittivity ($\varepsilon_{min}$) during a time period or window period ($\Delta t$). For example, the water detector 340 can determine that the permittivity difference satisfies the water detection threshold based on the permittivity difference being greater (e.g., substantially greater) than the water detection threshold. In some examples, the water detector 340 sets a flag (e.g., a water detection flag) when water is detected based on the permittivity, the permittivity difference, etc. As used herein, the flag is an indicator variable in computer and/or machine readable instructions.

In some examples, the water detector 340 compares a conductivity of the multiphase flow 104 to the water detection threshold and determines that water is present based on the comparison. For example, the water detector 340 can determine that the conductivity satisfies the water detection threshold based on the conductivity being greater (e.g., substantially greater) than the water detection threshold.

In some examples, the water detector 340 compares a conductivity difference to the water detection threshold and determines that water is present based on the comparison. For example, the conductivity difference can be a difference between a maximum conductivity ($\sigma_{max}$) and a minimum conductivity ($\sigma_{min}$) during a time period or window period ($\Delta t$). For example, the water detector 340 can determine that the conductivity difference satisfies the water detection threshold based on the conductivity difference being greater (e.g., substantially greater) than the water detection threshold. In some examples, the water detector 340 sets a flag (e.g., a water detection flag) when water is detected based on the conductivity, the conductivity difference, etc.

In the illustrated example of FIG. 3, the water detection manager 102 includes the report generator 350 to generate a report or a log associated with the multiphase flow 104 of FIG. 1. In some examples, the report generator 350 generates a report including one or more mixture parameters (e.g., the mixture parameters (1)-(8)) with respect to time or an oilfield operation. In some examples, the report generator 350 generates a report including a water detection determination result, a water detection occurrence frequency (e.g. a quantity of positive water detection flags per 60 s time period), water salinity, etc., and/or a combination thereof. For example, the report can include an indication that water is detected or not detected for one or more time periods (e.g., measurement time periods). In some examples, the report generator 350 generates an alert based on a value of a mixture parameter and/or a water detection determination result. For example, the report generator 350 can generate an alert (e.g., to flag the need to inject hydrate inhibitor, corrosion inhibitor, etc.) when water is detected in the multiphase flow 104. For example, the alert can include an indication that water is detected or not detected, a water detection occurrence frequency, and/or the salinity of water in the multiphase flow 104. In some examples, the report generator 350 transmits the report and/or the alert to another computing device communicatively coupled to the water detection manager 102 via the network 130.

In some examples, the report generator 350 can set a WLR measured by a multiphase flowmeter (e.g., a gamma-ray based multiple phase flowmeter (MPFM)) to zero based on a no water detection result (e.g., no water detected) in the multiphase flow 104. For example, the report generator 350 can set the WLR to zero to avoid and/or otherwise prevent a reporting of non-physical (e.g., negative) time-averaged WLR values to improve an accuracy in flow rate measurements of oil and gas phases made by the MPFM. For example, the report generator 350 can generate and transmit an alert indicating that water is not detected in the multiphase flow 104 to a MPFM communicatively coupled to the network 130. In response to receiving the alert, the MPFM or a control system communicatively coupled to the MPFM can set the WLR to zero. Alternatively, the MPFM may be communicatively coupled to the water detection manager 102 without the network 130 (e.g., the water detection manager is directly coupled to the MPFM).

In the illustrated example of FIG. 3, the water detection manager 102 includes the database 360 to record data (e.g., EM data, mixture parameters, water detection determination results, water salinity, excitation frequencies of the EM sensor(s) 124, 126, etc.). The database 360 can be implemented by a volatile memory (e.g., a Synchronous Dynamic Random Access Memory (SDRAM), Dynamic Random Access Memory (DRAM), RAMBUS Dynamic Random Access Memory (RDRAM), etc.) and/or a non-volatile memory (e.g., flash memory). The database 360 can additionally or alternatively be implemented by one or more double data rate (DDR) memories, such as DDR, DDR2, DDR3, mobile DDR (mDDR), etc. The database 360 can additionally or alternatively be implemented by one or more mass storage devices such as hard disk drive(s), compact disk drive(s) digital versatile disk drive(s), etc. While in the illustrated example the database 360 is illustrated as a single database, the database 360 can be implemented by any number and/or type(s) of databases. Furthermore, the data stored in the database 360 can be in any data format such as, for example, binary data, comma delimited data, tab delimited data, structured query language (SQL) structures, etc. In some examples, the database 360 can be cloud-based to enable synchronous retrieving and updating.

While an example manner of implementing the water detection manager 102 of FIG. 1 is illustrated in FIG. 3, one or more of the elements, processes, and/or devices illustrated in FIG. 3 may be combined, divided, re-arranged, omitted, eliminated, and/or implemented in any other way. Further, the example collection engine 310, the example measurement configurator 320, the example parameter calculator 330, the example water detector 340, the example report generator 350, the example database 360, and/or, more generally, the example water detection manager 102 of FIG. 1 may be implemented by hardware, software, firmware, and/or any combination of hardware, software, and/or firmware. Thus, for example, any of the example collection engine 310, the example measurement configurator 320, the example parameter calculator 330, the example water detector 340, the example report generator 350, the example database 360, and/or, more generally, the example water detection manager 102 could be implemented by one or more analog or digital circuit(s), logic circuits, programmable processor(s), programmable controller(s), graphics processing unit(s) (GPU(s)), digital signal processor(s) (DSP(s)), application specific integrated circuit(s) (ASIC(s)), programmable logic device(s) (PLD(s)), field programmable gate array(s) (FPGA(s)), and/or field programmable logic device(s) (FPLD(s)). When reading any of the apparatus or system claims of this patent to cover a purely software and/or firmware implementation, at least one of the example collection engine 310, the example measurement configurator 320, the example parameter calculator 330, the example water detector 340, the example report generator 350, and/or the example database 360 is/are hereby expressly defined to include a non-transitory computer readable storage device or storage disk such as a memory, a digital versatile disk (DVD), a compact disk (CD), a Blu-ray disk, etc., including the software and/or firmware. Further still, the example water detection manager 102 of FIG. 1 may include one or more elements, processes, and/or devices in addition to, or instead of, those illustrated in FIG. 3, and/or may include more than one of any or all of the illustrated elements, processes, and devices. As used herein, the phrase "in communication," including variations thereof, encompasses direct communication and/or indirect communication through one or more intermediary components, and does not require direct physical (e.g., wired) communication and/or constant communication, but rather additionally includes selective communication at periodic intervals, scheduled intervals, aperiodic intervals, and/or one-time events.

Figure 4:
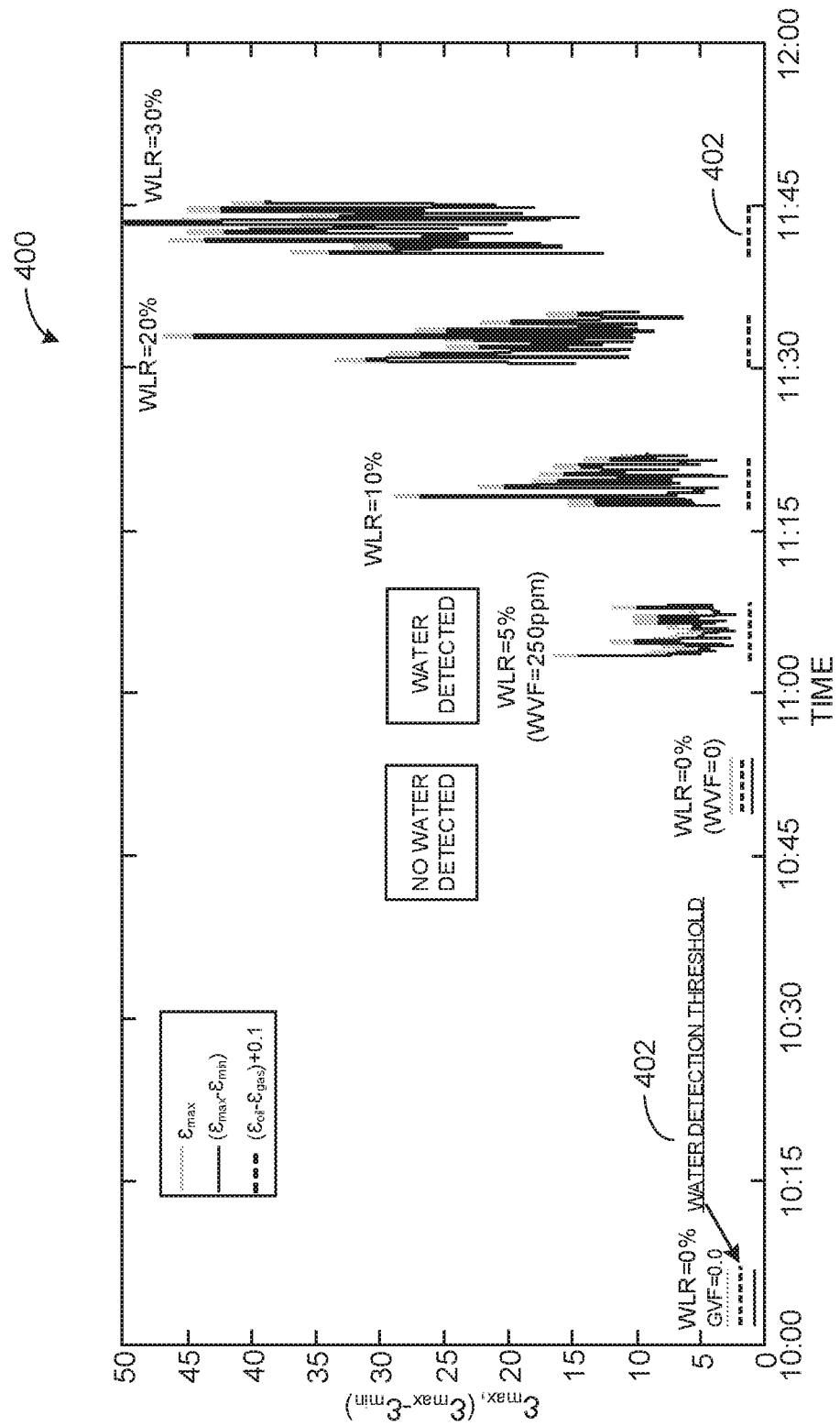
FIG. 4 depicts an example graph generated by the example water detection manager apparatus of FIGS. 1 and/or 3 to implement the examples disclosed herein.

FIG. 4 depicts an example graph 400 generated by the water detection manager 102 of FIGS. 1 and/or 3 to implement the examples disclosed herein. In FIG. 4, the water detection manager 102 generates the graph 400 based on a maximum permittivity ($\varepsilon_{max}$) and a permittivity difference ($\varepsilon_{max}-\varepsilon_{min}$) with respect to time. In FIG. 4, the graph 400 is based on the multiphase flow 104 of FIG. 1 where the multiphase flow 104 is a wet-gas flow with a GVF of 99.5% and with increasing WLR over time. In FIG. 4, the water detection manager 102 detects the presence of water when water-volume fraction (WVF) (e.g., WVF=WLR*(1−GVF)) is increased from a WVF of 0 to 250 parts per million (ppm) (and higher), by determining one or more mixture parameters, comparing the one or more mixture parameters to a threshold, and determining that the one more mixture parameters satisfy the threshold based on the comparison.

In the illustrated example of FIG. 4, the water detection manager 102 calculates mixture parameters including the maximum permittivity and the permittivity difference at a chosen or determined time interval (e.g., a determined relatively short time interval). For example, the water detection manager 102 can determine the mixture parameters every 100 ms, 500 ms, etc., based on raw EM data rapidly acquired at a data acquisition rate of 10 kHz from the EM sensor(s) 124, 126 of FIG. 1. In FIG. 4, the water detection manager 102 during a first example time period from 10:45 to 11:00 calculates values for the maximum permittivity and the permittivity difference and compares the values to an example water detection threshold 402.

In FIG. 4, the water detection threshold 402 is described below in Equation (1):

$$\text{water detection threshold} = (\varepsilon_{oil}-\varepsilon_{gas}) + \delta\varepsilon_{noise} \qquad \text{Equation (1)}$$

In the example of Equation (1) above, $\varepsilon_{oil}$ represents the permittivity of the oil phase of the multiphase flow 104, $\varepsilon_{gas}$ represents the permittivity of the gas phase of the multiphase flow 104, and $\delta\varepsilon_{noise}$ represents the permittivity noise. In FIG. 4, the permittivity noise is set to 0.1 to account for an uncertainty in oil/gas permittivity values. Alternatively, the permittivity noise may be set to any other value. In other examples, the permittivity noise is much less than 0.01 when related to the measured mixture permittivity standard deviation $\varepsilon_{std}(\Delta t)$ induced by measurement noise of the EM sensor(s) 124, 126 and/or EM electronics receiving the EM data from the EM sensor(s) 124, 126 (e.g., the collection engine 310 of FIG. 3). For example, measurement noise in the EM sensor(s) 124, 126 and/or EM electronics can be determined based on the permittivity average and standard deviation values when performing static gas or static oil measurements.

In the illustrated example of FIG. 4, the water detection manager 102 determines that no water is detected during the time period 10:45 to 11:00 based on the permittivity difference ($\varepsilon_{max}-\varepsilon_{min}$) not being greater than the water detection threshold 402. In FIG. 4, the water detection manager 102 determines that water is detected during the time periods of 11:00 to 11:15, 11:15 to 11:30, and 11:30 to 11:45 by determining that the permittivity difference is greater than the water detection threshold 402. In some examples, the increasing permittivity difference ($\varepsilon_{max}-\varepsilon_{min}$) indicates an increase in the liquid WLR.

Figure 6:
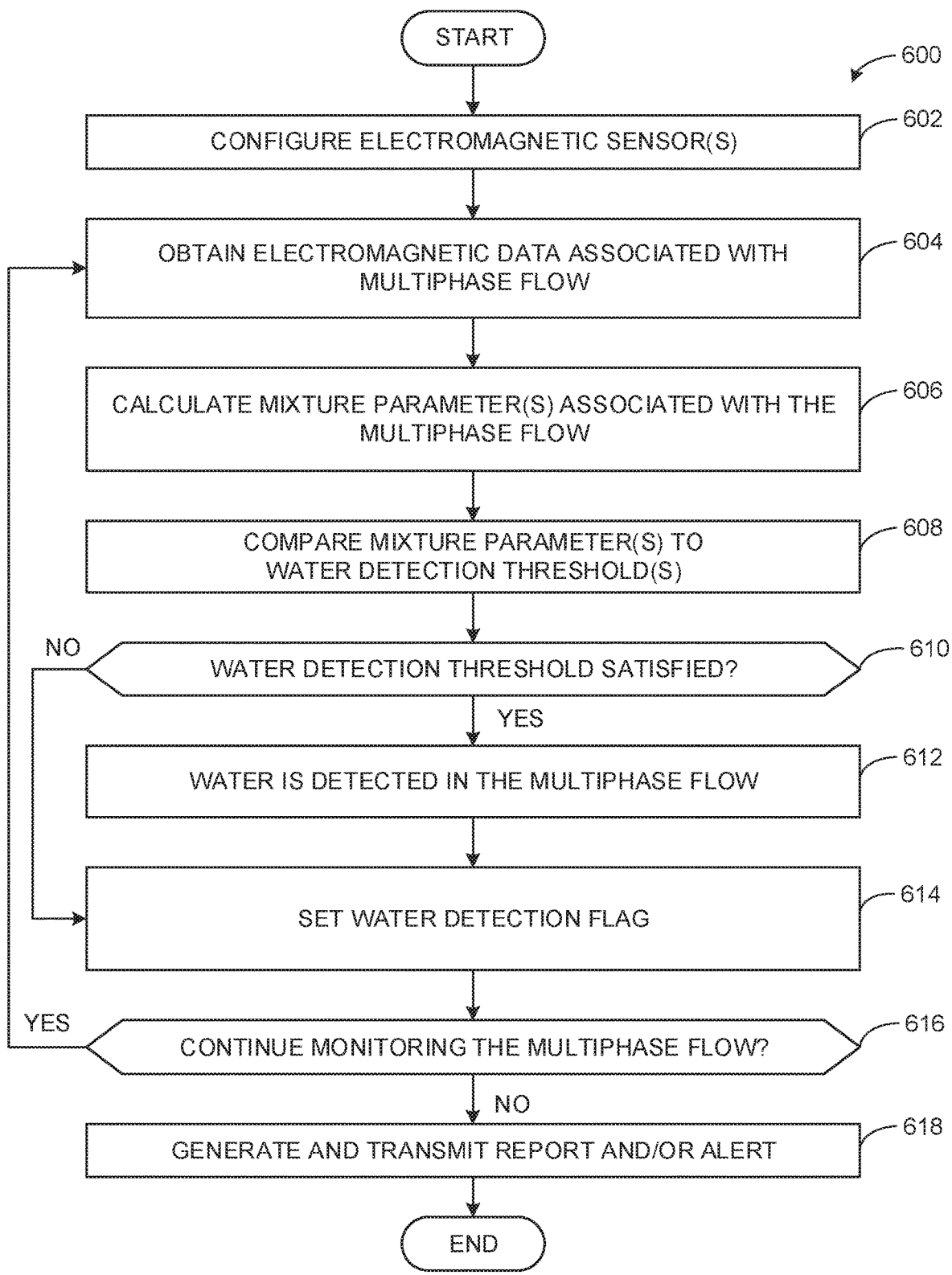
FIG. 6 is a flowchart representative of machine readable instructions that may be executed to implement the example water detection manager apparatus of FIGS. 1 and/or 3.

Flowcharts representative of example hardware logic, machine readable instructions, hardware implemented state machines, and/or any combination thereof for implementing the water detection manager 102 of FIGS. 1 and/or 3 are shown in FIGS. 5-6. The machine readable instructions may be an executable program or portion of an executable program for execution by a computer processor such as the processor 712 shown in the example processor platform 700 discussed below in connection with FIG. 7. The program may be embodied in software stored on a non-transitory computer readable storage medium such as a CD-ROM, a floppy disk, a hard drive, a DVD, a Blu-ray disk, or a memory associated with the processor 712, but the entire program and/or parts thereof could alternatively be executed by a device other than the processor 712 and/or embodied in firmware or dedicated hardware. Further, although the example program is described with reference to the flowcharts illustrated in FIGS. 5-6, many other methods of implementing the example water detection manager 102 may alternatively be used. For example, the order of execution of the blocks may be changed, and/or some of the blocks described may be changed, eliminated, or combined. Additionally or alternatively, any or all of the blocks may be implemented by one or more hardware circuits (e.g., discrete and/or integrated analog and/or digital circuitry, an FPGA, an ASIC, a comparator, an operational-amplifier (op-amp), a logic circuit, etc.) structured to perform the corresponding operation without executing software or firmware.

As mentioned above, the example processes of FIGS. 5-6 may be implemented using executable instructions (e.g., computer and/or machine readable instructions) stored on a non-transitory computer and/or machine readable medium such as a hard disk drive, a flash memory, a read-only memory, a compact disk, a digital versatile disk, a cache, a random-access memory, and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media.

"Including" and "comprising" (and all forms and tenses thereof) are used herein to be open ended terms. Thus, whenever a claim employs any form of "include" or "comprise" (e.g., comprises, includes, comprising, including, having, etc.) as a preamble or within a claim recitation of any kind, it is to be understood that additional elements, terms, etc. may be present without falling outside the scope of the corresponding claim or recitation. As used herein, when the phrase "at least" is used as the transition term in, for example, a preamble of a claim, it is open-ended in the same manner as the term "comprising" and "including" are open ended. The term "and/or" when used, for example, in a form such as A, B, and/or C refers to any combination or subset of A, B, C such as (1) A alone, (2) B alone, (3) C alone, (4) A with B, (5) A with C, (6) B with C, and (7) A with B and with C.

FIG. 5 depicts example source code 500 representative of example computer readable instructions that can be executed to implement the example water detection manager 102 of FIGS. 1 and/or 3 that can be used to implement the examples disclosed herein. For example, the source code 500 can be used to implement the process of FIG. 6. In the source code 500, the water detection manager 102 executes an example function or process (int getWaterDetection) to determine whether water is detected in the multiphase flow 104 of FIG. 1.

In the source code 500 of FIG. 5, the water detection manager 102 makes water detection determination results immune to potentially small drifts in the multiphase flow measurement system 100 by comparing one or more mixture parameters to at least two different water detection thresholds. For example, the water detection manager 102 immunizes potential drifts in one or both EM sensors 124, 126 of FIG. 1, EM sensor electronics included in the water detection manager 102, etc., by comparing the one or more mixture parameters to at least two different water detection thresholds as depicted in the source code 500.

In the source code 500 of FIG. 5, the water detection manager 102 compares a permittivity difference during a time window $\Delta t$ ($\varepsilon_{max}(\Delta t)-\varepsilon_{min}(\Delta t)$) to a first water detection threshold (($\varepsilon_{oil}(p,T)-\varepsilon_{gas}(p,T))+\delta\varepsilon_{noise}$) determined at the measured multiphase-flow pressure p and temperature T. For example, the water detector 340 of FIG. 3 can compare the permittivity difference to the first water threshold and determine that water is present in the multiphase flow 104 based on the comparison.

The water detection manager 102 uses the mixture permittivity maximum ($\varepsilon_{max}(\Delta t)$) to capture a water-rich data point and uses the mixture permittivity minimum ($\varepsilon_{min}(\Delta t)$) to capture a gas-rich data point for, in some examples, at least 1000 data points rapidly acquired during the time window $\Delta t$. In the source code 500, oil and gas permittivity pressure-volume-temperature (PVT) models are used to track the changes in the oil permittivity ($\varepsilon_{oil}(p,T)$ and the gas permittivity ($\varepsilon_{gas}(p,T)$) of the multiphase flow 104. The PVT models are generated based on obtaining and/or otherwise determining the densities and chemical compositions of the oil and gas included in the multiphase flow 104. For example, the densities and chemical compositions can be determined by performing gas chromatograph analysis of samples of oil and gas included in the multiphase flow 104.

In the source code 500 of FIG. 5, if the water detection manager 102 determines that the permittivity difference is greater than the first water detection threshold, then the water detection manager 102 sets the water detection flag (waterDetectionFlag) to true indicating that water is present in the multiphase flow 104. If the water detection manager 102 determines that the permittivity difference is not greater than the first water detection threshold, then the water detection manager 102 compares the maximum permittivity during the time window ($\varepsilon_{max}(\Delta t)$) to a second water detection threshold ($\varepsilon_{oil}(p,T)+\delta\varepsilon_{oil}$). In some examples, the uncertainty in the oil permittivity ($\delta\varepsilon_{oil}$) is chosen to include an absolute (RF electronics) baseline drift in the permittivity measurement (e.g., by choosing $\delta\varepsilon_{oil}$ to be in a range of 1.0 to 1.5).

In the source code 500 of FIG. 5, if the water detection manager 102 determines that the maximum permittivity is greater than the second water detection threshold, then the water detection manager 102 sets the water detection flag to true indicating that water is present in the multiphase flow 104. If the water detection manager 102 determines that the maximum permittivity is not greater than the second water detection threshold, then the water detection manager 102 sets the water detection flag to false indicating that water is absent from and/or otherwise present in a negligible amount in the multiphase flow 104. In response to setting the water detection flag, the source code 500 returns a value of the water detection flag. In some examples, the quantity of true water detection occurrences can be accumulated over a specified time duration (e.g., every 10 s, every 60 s, etc.) to calculate and/or otherwise determine a water detection occurrence frequency.

FIG. 6 is a flowchart representative of example machine readable instructions 600 that can be executed to implement the water detection manager 102 of FIGS. 1 and/or 3 to detect a presence of water in the multiphase flow 104 of FIG. 1. The machine readable instructions 600 begin at block 602, at which the water detection manager 102 configures electromagnetic sensor(s). For example, the measurement configurator 320 of FIG. 3 can configure one or both EM sensors 124, 126 of FIG. 1 to excite EM energy into the multiphase flow 104 at a specified RF/microwave frequency.

At block 604, the water detection manager 102 obtains electromagnetic data associated with a multiphase flow. For example, the collection engine 310 of FIG. 3 can obtain EM data from one or both EM sensors 124, 126 associated with the multiphase flow 104.

At block 606, the water detection manager 102 calculates mixture parameter(s) associated with the multiphase flow. For example, the parameter calculator 330 can calculate one or more of the mixture parameters (1)-(8) as described above.

At block 608, the water detection manager 102 compares mixture parameter(s) to water detection threshold(s). For example, the water detector 340 can compare the permittivity difference to the first water detection threshold as described above in connection with the source code 500 of FIG. 5. In other examples, the water detector 340 can compare the maximum permittivity to the second water detection threshold as described above in connection with the source code 500 of FIG. 5.

At block 610, the water detection manager 102 determines whether a water detection threshold has been satisfied. For example, the water detector 340 can determine that the permittivity difference satisfies the first water detection threshold based on the difference. In such examples, the water detector 340 can determine that the first water detection threshold is satisfied based on the permittivity difference being greater than the first water detection threshold.

If, at block 610, the water detection manager 102 determines that the water detection threshold has not been satisfied, control proceeds to block 614 to set a water detection flag. For example, the water detector 340 can set the water detection flag to false indicating that water is not detected in the multiphase flow 104. If, at block 610, the water detection manager 102 determines that the water detection threshold has been satisfied, then, at block 612, the water detection manager 102 detects water in the multiphase flow. For example, the water detector 340 can determine that water is detected in the multiphase flow 104.

In response to detecting water in the multiphase flow, the water detection manager 102 sets the water detection flag at block 614. For example, the water detector 340 can set the water detection flag to true indicating that water is detected in the multiphase flow 104. In response to setting the water detection flag at block 614, the water detection manager 102 determines whether to continue monitoring the multiphase flow at block 616. For example, the collection engine 310 can determine to continue obtaining EM data from the EM sensor(s) 124, 126 associated with the multiphase flow 104.

If, at block 616, the water detection manager 102 determines to continue monitoring the multiphase flow, control returns to block 604 to obtain electromagnetic data associated with the multiphase flow. If, at block 616, the water detection manager 102 determines not to continue monitoring the multiphase flow, then, at block 618, the water detection manager 102 generates and transmits a report and/or an alert. For example, the report generator 350 can generate a report including the water detection determination result (e.g., a value of the water detection flag), one or more mixture parameters, the graph 400 of FIG. 4, etc., and/or a combination thereof. In such examples, the report generator 350 can generate an alert indicating whether water is detected in the multiphase flow 104. In such examples, the report generator 350 can transmit the report and/or the alert to an external computing device via the network 130 of FIG. 1. In such examples, a MPFM communicatively coupled to the network 130 can set a WLR used by the MPFM to calculate flow rate measurements of the multiphase flow 104 to zero when water is not detected for a relatively long duration (e.g. every 60 s, every 300 s, etc.) to improve an accuracy of the calculated measurements.

In response to generating and transmitting the report and/or the alert, the machine readable instructions 600 conclude. Alternatively, the machine readable instructions 600 can be executed using mixture parameters based on mixture conductivity data (e.g., $\sigma_{min}(\Delta t)$, $\sigma_{max}(\Delta t)$, etc.) when water with a conductivity value larger than a threshold is used (e.g., a threshold of 0.5 S/m, 1.0 S/m, 1.5 S/m, etc.).

Figure 7:
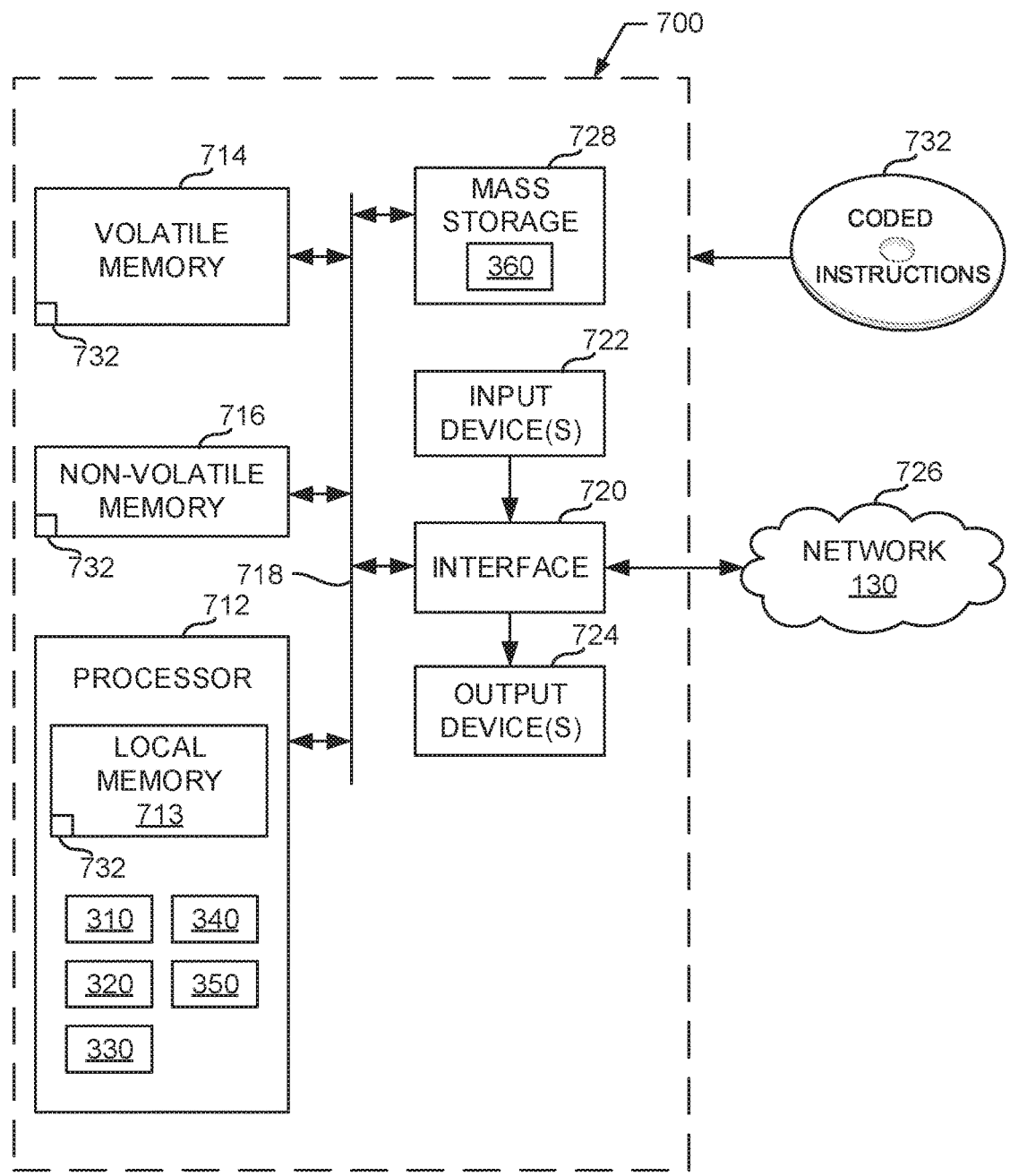
FIG. 7 is a block diagram of an example processing platform structured to execute the instructions of FIGS. 5 and/or 6 to implement the example water detection manager apparatus of FIGS. 1 and/or 3.

FIG. 7 is a block diagram of an example processor platform 700 structured to execute the instructions of FIGS. 5-6 to implement the water detection manager 102 of FIGS. 1 and/or 3. The processor platform 700 can be, for example, a server, a personal computer, a workstation, a self-learning machine (e.g., a neural network), a mobile device (e.g., a cell phone, a smart phone, a tablet such as an iPad™), a personal digital assistant (PDA), an Internet appliance, a headset or other wearable device, or any other type of computing device.

The processor platform 700 of the illustrated example includes a processor 712. The processor 712 of the illustrated example is hardware. For example, the processor 712 can be implemented by one or more integrated circuits, logic circuits, microprocessors, GPUs, DSPs, or controllers from any desired family or manufacturer. The hardware processor may be a semiconductor based (e.g., silicon based) device. In this example, the processor 712 implements the example collection engine 310, the example measurement configurator 320, the example parameter calculator 330, the example water detector 340, and the example report generator 350 of FIG. 3.

The processor 712 of the illustrated example includes a local memory 713 (e.g., a cache). The processor 712 of the illustrated example is in communication with a main memory including a volatile memory 714 and a non-volatile memory 716 via a bus 718. The volatile memory 714 may be implemented by Synchronous Dynamic Random Access Memory (SDRAM), Dynamic Random Access Memory (DRAM), RAMBUS® Dynamic Random Access Memory (RDRAM®), and/or any other type of random access memory device. The non-volatile memory 716 may be implemented by flash memory and/or any other desired type of memory device. Access to the main memory 714, 716 is controlled by a memory controller.

The processor platform 700 of the illustrated example also includes an interface circuit 720. The interface circuit 720 may be implemented by any type of interface standard, such as an Ethernet interface, a universal serial bus (USB), a Bluetooth® interface, a near field communication (NFC) interface, and/or a PCI express interface.

In the illustrated example, one or more input devices 722 are connected to the interface circuit 720. The input device(s) 722 permit(s) a user to enter data and/or commands into the processor 712. The input device(s) 722 can be implemented by, for example, an audio sensor, a microphone, a camera (still or video), a keyboard, a button, a mouse, a touchscreen, a track-pad, a trackball, an isopoint device, and/or a voice recognition system.

One or more output devices 724 are also connected to the interface circuit 720 of the illustrated example. The output devices 724 can be implemented, for example, by display devices (e.g., a light emitting diode (LED), an organic light emitting diode (OLED), a liquid crystal display (LCD), a cathode ray tube display (CRT), an in-place switching (IPS) display, a touchscreen, etc.), a tactile output device, a printer, and/or speaker. The interface circuit 720 of the illustrated example, thus, typically includes a graphics driver card, a graphics driver chip, and/or a graphics driver processor.

The interface circuit 720 of the illustrated example also includes a communication device such as a transmitter, a receiver, a transceiver, a modem, a residential gateway, a wireless access point, and/or a network interface to facilitate exchange of data with external machines (e.g., computing devices of any kind) via a network 726. The communication can be via, for example, an Ethernet connection, a digital subscriber line (DSL) connection, a telephone line connection, a coaxial cable system, a satellite system, a line-of-site wireless system, a cellular telephone system, etc. The network 726 implements the example network 130 of FIGS. 1 and/or 3.

The processor platform 700 of the illustrated example also includes one or more mass storage devices 728 for storing software and/or data. Examples of such mass storage devices 728 include floppy disk drives, hard drive disks, compact disk drives, Blu-ray disk drives, redundant array of independent disks (RAID) systems, and digital versatile disk (DVD) drives.

The machine executable instructions 732 of FIGS. 5-6 may be stored in the mass storage device 728, in the volatile memory 714, in the non-volatile memory 716, and/or on a removable non-transitory computer readable storage medium such as a CD or DVD.

In the specification and appended claims: the terms "connect," "connection," "connected," "in connection with," and "connecting" are used to mean "in direct connection with" or "in connection with via one or more elements;" and the term "set" is used to mean "one element" or "more than one element." Further, the terms "couple," "coupling," "coupled," "coupled together," and "coupled with" are used to mean "directly coupled together" or "coupled together via one or more elements." As used herein, the terms "up" and "down," "upper" and "lower," "upwardly" and "downwardly," "upstream" and "downstream;" "above" and "below;" and other like terms indicating relative positions above or below a given point or element are used in this description to more clearly describe some embodiments of the disclosure.

From the foregoing, it will be appreciated that example methods, apparatus, and systems have been disclosed that detect water in multiphase flows. The above-disclosed examples describe detecting the presence of water in a multiphase or a wet-gas flow stream by interpreting mixture parameters including mixture permittivity and/or mixture conductivity obtained at high data sampling or acquisition frequencies by one or more electromagnetic sensors. The above-disclosed examples improve an accuracy of flow rate measurements of individual phases of the multiphase flow by setting a WLR to zero when water is not detected in the multiphase flow. The above-disclosed examples also improve flow assurance and/or water processing facility planning of oilfield gas-oil production operations, by transmitting alert of the risks of hydrate formation (blockage) and/or corrosions in the flowline when water is detected in the multiphase flow. Alternatively, the above-disclosed methods and apparatus can be applicable to other electromagnetic measurement techniques, such as sensors based on (local) RF/microwave transmission measurement, (local) electrical impedance (e.g., capacitance, conductance, inductance, etc.) measurement, etc., and/or a combination thereof.

Example 1 includes an apparatus, comprising a conduit including an inlet to receive a multiphase flow, and an electromagnetic sensor coupled to a liquid-rich region of the conduit to measure a permittivity of the multiphase flow, and a water detection manager to determine that water is detected in the multiphase flow based on the permittivity.

Example 2 includes the apparatus of example 1, wherein the liquid-rich region is disposed at an underside of a horizontal blind tee conduit or disposed at a near-wall region of a vertical conduit.

Example 3 includes the apparatus of example 1, wherein the electromagnetic sensor is a radiofrequency (RF) or a microwave frequency open-coaxial probe, an rf/microwave local transmission measurement sensor, an rf/microwave local resonance sensor, a millimeter-wave sensor, or an electrical impedance local measurement sensor, the electromagnetic sensor to operate at one measurement frequency or a plurality of measurement frequencies.

Example 4 includes the apparatus of example 1, wherein the permittivity is a first permittivity, the water detection manager further including a parameter calculator to determine the first permittivity and a second permittivity of the multiphase flow based on electromagnetic data obtained from the electromagnetic sensor, and a water detector to compare a difference between the first permittivity and the second permittivity to a water detection threshold, and determine that water is detected in the multiphase flow based on the comparison.

Example 5 includes the apparatus of example 4, further including a report generator to generate a report including at least one of the first permittivity, the second permittivity, or an indication that water is detected in the multiphase flow.

Example 6 includes the apparatus of example 4, further including a report generator to generate an alert indicating that water is not detected in the multiphase flow, the alert causing a water-to-liquid ratio to be set to zero for a flowmeter measuring the multiphase flow.

Example 7 includes a method, comprising determining a first permittivity and a second permittivity of a multiphase flow based on electromagnetic data obtained from an electromagnetic sensor, comparing a difference between the first permittivity and the second permittivity to a water detection threshold, and in response to the difference satisfying the water detection threshold, generating an alert indicating that water is present in the multiphase flow.

Example 8 includes the method of example 7, wherein the electromagnetic sensor is measuring a liquid-rich region disposed at an underside of a horizontal blind tee conduit or disposed at a near-wall region of a vertical conduit.

Example 9 includes the method of example 7, wherein the electromagnetic sensor is a radiofrequency (RF) or microwave frequency open-coaxial probe, an rf/microwave local transmission measurement sensor, an rf/microwave local resonance sensor, a millimeter-wave sensor, or an electrical impedance local measurement sensor.

Example 10 includes the method of example 9, wherein the electromagnetic sensor operates at one measurement frequency or a plurality of measurement frequencies.

Example 11 includes the method of example 7, further including in response to the difference satisfying the water detection threshold, generating a report including at least one of the first permittivity, the second permittivity, or an indication that water is detected in the multiphase flow.

Example 12 includes the method of example 7, further including in response to determining that water is absent in the multiphase flow, causing a water-to-liquid ratio to be set to zero for a flowmeter measuring the multiphase flow.

Example 13 includes the method of example 7, wherein the water detection threshold is a first water detection threshold, and further including comparing the first permittivity to a second water detection threshold, and in response to the first permittivity satisfying the second water detection threshold, generating an alert indicating that water is detected in the multiphase flow based on the comparison.

Example 14 includes the method of example 13, further including in response to determining that water is detected in the multiphase flow, generating a report including at least one of the first permittivity and an indication that water is detected in the multiphase flow.

Example 15 includes a non-transitory computer readable storage medium comprising instructions which, when executed, causes a machine to at least determine a first permittivity and a second permittivity of a multiphase flow based on electromagnetic data obtained from an electromagnetic sensor, compare a difference between the first permittivity and the second permittivity to a water detection threshold, and generate an alert indicating that water is detected in the multiphase flow when the difference satisfies the water detection threshold.

Example 16 includes the non-transitory computer readable storage medium of example 15, wherein the electromagnetic sensor is a radiofrequency (RF) or microwave frequency open-coaxial probe, an rf/microwave local transmission measurement sensor, an rf/microwave local resonance sensor, a millimeter-wave sensor, or an electrical impedance local measurement sensor, the electromagnetic sensor to operate at one measurement frequency or a plurality of measurement frequencies.

Example 17 includes the non-transitory computer readable storage medium of example 15, further including instructions which, when executed, cause the machine to at least generate a report including at least one of the first permittivity, the second permittivity, or an indication that water is detected in the multiphase flow when the difference satisfies the water detection threshold.

Example 18 includes the non-transitory computer readable storage medium of example 15, further including instructions which, when executed, cause the machine to at least cause a water-to-liquid ratio to be set to zero for a flowmeter measuring the multiphase flow when water is not detected in the multiphase flow.

Example 19 includes the non-transitory computer readable storage medium of example 15, wherein the water detection threshold is a first water detection threshold, and further including instructions which, when executed, cause the machine to at least compare the first permittivity to a second water detection threshold, and generate an alert indicating that water is detected in the multiphase flow based on the comparison when the first permittivity satisfies the second water detection threshold.

Example 20 includes the non-transitory computer readable storage medium of example 19, further including instructions which, when executed, cause the machine to at least generate a report including at least one of the first permittivity and an indication that water is not detected in the multiphase flow when water is not detected in the multiphase flow.

Although the preceding description has been described herein with reference to particular means, materials and embodiments, it is not intended to be limited to the particulars disclosed herein; rather, it extends to all functionally equivalent structures, methods, and uses, such as are within the scope of the appended claims.

The invention claimed is:

1. An apparatus, comprising:
a conduit including:
an inlet to receive a multiphase flow;
an electromagnetic sensor coupled to a liquid-rich region of the conduit to obtain a plurality of permittivity measurements of the multiphase flow; and
a water detection manager to determine that water is detected in the multiphase flow based on the plurality of permittivity measurements, the water detection manager including:
a parameter calculator to determine a maximum of the plurality of permittivity measurements and a minimum of the plurality of permittivity measurements, and a difference between the maximum and the minimum; and
a water detector to:
compare the difference to a water detection threshold; and
determine that water is detected in the multiphase flow based on the comparison.

2. The apparatus of claim 1, wherein the liquid-rich region is disposed at an underside of a horizontal blind tee conduit or disposed at a near-wall region of a vertical conduit.

3. The apparatus of claim 1, wherein the electromagnetic sensor is a radiofrequency (RF) or a microwave frequency open-coaxial probe, an RF/microwave local transmission measurement sensor, an RF/microwave local resonance sensor, a millimeter-wave sensor, or an electrical impedance local measurement sensor, the electromagnetic sensor to operate at one measurement frequency or a plurality of measurement frequencies.

4. The apparatus of claim 1, further including a report generator to generate a report including at least one of the maximum permittivity, the minimum permittivity, or an indication that water is detected in the multiphase flow.

5. The apparatus of claim 1, further including a report generator to generate an alert indicating that water is not detected in the multiphase flow, the alert causing a water-to-liquid ratio to be set to zero for a flowmeter measuring the multiphase flow.

6. A method, comprising:
determining a maximum permittivity and a minimum permittivity of a multiphase flow during a measurement duration based on electromagnetic data obtained from an electromagnetic sensor;
comparing a difference between the maximum permittivity and the minimum permittivity to a water detection threshold; and
in response to the difference satisfying the water detection threshold, generating an alert indicating that water is present in the multiphase flow.

7. The method of claim 6, wherein the electromagnetic sensor is measuring a liquid-rich region disposed at an underside of a horizontal blind tee conduit or disposed at a near-wall region of a vertical conduit.

8. The method of claim 6, wherein the electromagnetic sensor is a radiofrequency (RF) or microwave frequency open-coaxial probe, an RF/microwave local transmission measurement sensor, an RF/microwave local resonance sensor, a millimeter-wave sensor, or an electrical impedance local measurement sensor.

9. The method of claim 8, wherein the electromagnetic sensor operates at one measurement frequency or a plurality of measurement frequencies.

10. The method of claim 6, further including in response to the difference satisfying the water detection threshold, generating a report including at least one of the maximum permittivity, the minimum permittivity, or an indication that water is detected in the multiphase flow.

11. The method of claim 6, further including in response to determining that water is absent in the multiphase flow, causing a water-to-liquid ratio to be set to zero for a flowmeter measuring the multiphase flow.

12. The method of claim 6, wherein the water detection threshold is a first water detection threshold, and further including:
comparing the maximum permittivity to a second water detection threshold; and in response to the maximum permittivity satisfying the second water detection threshold, generating an alert indicating that water is detected in the multiphase flow based on the comparison.

13. The method of claim 12, further including in response to determining that water is detected in the multiphase flow, generating a report including at least one of the maximum permittivity and an indication that water is detected in the multiphase flow.

14. A non-transitory computer readable storage medium comprising instructions which, when executed, causes a machine to at least:
determine a maximum permittivity and a minimum permittivity of a multiphase flow based on electromagnetic data obtained from an electromagnetic sensor during a measurement duration;
compare a difference between the maximum permittivity and the minimum permittivity to a water detection threshold; and
generate an alert indicating that water is detected in the multiphase flow when the difference satisfies the water detection threshold.

15. The non-transitory computer readable storage medium of claim 14, wherein the electromagnetic sensor is a radiofrequency (RF) or microwave frequency open-coaxial probe, an RF/microwave local transmission measurement sensor, an RF/microwave local resonance sensor, a millimeter-wave sensor, or an electrical impedance local measurement sensor, the electromagnetic sensor to operate at one measurement frequency or a plurality of measurement frequencies.

16. The non-transitory computer readable storage medium of claim 14, further including instructions which, when executed, cause the machine to at least generate a report including at least one of the maximum permittivity, the minimum permittivity, or an indication that water is detected in the multiphase flow when the difference satisfies the water detection threshold.

17. The non-transitory computer readable storage medium of claim 14, further including instructions which, when executed, cause the machine to at least cause a water-to-liquid ratio to be set to zero for a flowmeter measuring the multiphase flow when water is not detected in the multiphase flow.

18. The non-transitory computer readable storage medium of claim 14, wherein the water detection threshold is a first water detection threshold, and further including instructions which, when executed, cause the machine to at least:
compare the maximum permittivity to a second water detection threshold; and
generate an alert indicating that water is detected in the multiphase flow based on the comparison when the maximum permittivity satisfies the second water detection threshold.

19. The non-transitory computer readable storage medium of claim 18, further including instructions which, when executed, cause the machine to at least generate a report including at least one of the maximum permittivity and an indication that water is not detected in the multiphase flow when water is not detected in the multiphase flow.

* * * * *